United States Patent [19]

Hammerle

[11] Patent Number: 4,741,200
[45] Date of Patent: May 3, 1988

[54] METHOD AND APPARATUS FOR MEASURING VISCOSITY IN A LIQUID UTILIZING A PIEZOELECTRIC SENSOR

[75] Inventor: Robert H. Hammerle, Franklin, Mich.

[73] Assignee: Ford Motor Company, Dearborn, Mich.

[21] Appl. No.: 884,824

[22] Filed: Jul. 11, 1986

[51] Int. Cl.⁴ ............................................. G01N 11/16
[52] U.S. Cl. ........................................ 73/54; 310/369
[58] Field of Search ................ 73/54, 32 A; 310/369, 310/333

[56] References Cited

U.S. PATENT DOCUMENTS

| | | | |
|---|---|---|---|
| 3,194,064 | 7/1965 | Miles | 73/54 X |
| 3,903,731 | 9/1975 | Sieben | 73/54 |
| 3,903,732 | 9/1975 | Rork et al. | 73/54 |
| 3,943,753 | 3/1976 | Simon | 73/54 |
| 3,967,490 | 7/1976 | Brady | 73/32 A |
| 4,063,448 | 12/1977 | Agar | 73/32 A |
| 4,262,227 | 4/1981 | Ikeno et al. | 310/369 X |
| 4,370,584 | 1/1983 | Ikeno et al. | 310/369 X |
| 4,524,610 | 6/1985 | Fitzgerald et al. | 73/54 |

FOREIGN PATENT DOCUMENTS 913165  3/1982  U.S.S.R. ................... 73/54

OTHER PUBLICATIONS

Fisch, M. R. et al., *Improved Acoustic Viscosimeter Technique*, In. J. Acoust. Soc. Am., vol. 60, No. 3, pp. 623–625, Sep. 1976.
Piezoelectric Crystals and Their Application to Utrasonics; by Warren P. Mason, PH.D., pp. 339–350.
Frequency of a Quartz Microbalance in Contact With Liquid, by K. K. Kanagawa et al., Anal. Chem., 57 (1985), pp. 1770–1777.

Primary Examiner—Stewart J. Levy
Assistant Examiner—Joseph W. Roskos
Attorney, Agent, or Firm—Paul K. Godwin, Jr.; Clifford L. Sadler

[57] ABSTRACT

A piezoelectric element energized to exhibit thickness-shear mode vibration is utilized to measure the viscosity of liquids. Electrodes, of an inert material are bonded to the major faces of the disc shaped crystal and are of a lesser diameter than the crystal surfaces so as to provide a concentric ring area of the crystal that is unenergized.

11 Claims, 2 Drawing Sheets

METHOD AND APPARATUS FOR MEASURING VISCOSITY IN A LIQUID UTILIZING A PIEZOELECTRIC SENSOR

BACKGROUND OF THE INVENTION

1. Field of the Invention

This invention relates to the field of measuring liquid viscosity and more specifically to the area in which such measurements are made by utilizing a piezoelectric sensor element.

2. Description of the Prior Art

Viscosity measurements utilizing piezoelectric sensors are generally based on the well-known phenomenon that a dissipative or damping force that resists the motion of an energized piezoelectric element lowers its resonant frequency.

Viscosity measurements have been made routinely in the past by using torsional crystals. Such techniques are described in a text by W. P. Mason, entitled "Piezoelectric Crystals and Their Application to Ultrasonics", D. Van Nostrand Company, Princeton, N.J., 1950, pages 339–350. Torsional crystals are described as being formed from ammonium dihydrogen phosphate ADP. The crystals are cut to have a length dimension defined along the "X" axis. A hole is bored along the "X" axis and a cylindrical crystal is formed by turning it about the center of the bore. The crystal is plated with an electrically conducting material continuously over the inner surface and with a strip lengthwise on the outer surface to form the inner and outer electrodes for energizing the crystal. The sensor is shown as being permanently mounted in a liquid container and filled with the liquid to be measured. Due to size limitations in constructing the torsional vibrating crystals, it has been found that the frequency limit is approximately 500 KHz.

The Mason text also describes (page 349) attempts to measure liquid viscosity using thickness-shear mode crystals, like AT cut quartz. However, the measurements were hindered by the tendency of the elements to vibrate in flexural modes. Consequently it was concluded that since it was difficult to distinguish the viscosity controlled shear mode from the flexural modes it was also difficult to unambiguously determine the viscosity of liquid. In addition, flexural oscillations have longitudinal components that generate sound waves in the liquid. These waves can contribute a substantial additional energy dissipation from the motion of the element as such waves radiate into the liquid and interact with the container. The extent of the dissipation depends on the exact position of the element in the container. Therefore, if the element position is changed, the resonant frequencies of the flexural modes change and thereby further obscure the viscosity-controlled thickness-shear mode.

An attempt to measure the viscosity of sucrose and water solutions using thickness-shear mode crystals was described in an article entitle "Frequency of a Quartz Microbalance in Contact With Liquid", by K. K. Kanazawa et al, appearing in ANAL. CHEM., 57, 1770 (1985). That configuration has the disadvantage of a drag being imposed on the element which increases when the pressure differential across the element increases. Thus, the resonant frequency of that structure depends on the depth of its submersion into the liquid.

SUMMARY OF THE INVENTION

It is an object of the present invention to essentially eliminate the flexural vibrations of a piezoelectric crystal in liquid by using a piezoelectric disc shaped elements including variable thickness discs such as convex or plano-convex surfaced elements that have only the center portions of the major surfaces covered with electrodes. Piezoelectric elements of this type are called "trapped vibrators".

The disc shaped piezoelectric element is thus caused to vibrate in its thickness-shear mode. The thickness-shear mode crystals have two main advantages over torsional mode crystals for the measurement of liquid viscosity. The first advantage arises due to the simplicity of construction of the actual sensor element as a disc element rather than a cylindrical element. Secondly, due to the smaller size availability, the thickness-shear mode crystals may be operated at significantly higher frequencies. Such higher frequencies are necessary for measuring viscosities at very high shear rates. For instance, lubricating liquids used in internal combustion engines are subject to shear rates typically on the order of 1–10 MHz. Higher frequencies are necessary in studying the properties of polymeric materials.

In the present invention, a disc shaped shear mode crystal is made to operate in a "trapped" shear mode by utilizing thin film electrodes mounted on opposing surfaces of the disc shaped crystal so as to leave an outer concentric ring which is not subject to shear mode energization. The opposing electrodes each contain a portion which extends to the outer periphery of the crystal in a direction diametrically opposite to the other. The extensions are correspondingly connected at the edge of the disc with supporting lead wires. The supporting lead wires are in turn connected to an insulated member for support. In this manner, the vibrating central portion of the disc is not subject to loading by the support wires. The only loading is due to the electrode mass and the environment surrounding the surfaces to effect the shear mode movement of the surfaces beneath the opposing electrodes, with respect to each other. The sensor is electrically connected to an oscillator which has an adjustable and calibrated output frequency so as to energize the shear mode crystal.

A detecting means is also provided in order that electrical characteristics of the shear mode crystal may be monitored and provide an indication as to when the shear mode crystal reaches its resonance in response to a particular drive frequency.

The method of measuring viscosity in liquid involves providing the aforementioned apparatus and comparing the resonant frequency of the shear mode crystal in a standard liquid medium or air to that which is determined in a particular liquid to be tested.

A chart is shown whereby known samples of liquid having known viscosities were used to calibrate the apparatus so that future measurements of unknown liquids, using the aforementioned method, will produce a quantified value of viscosity.

DETAILED DESCRIPTION OF THE PREFERRED EMBODIMENT

Figure 1A:
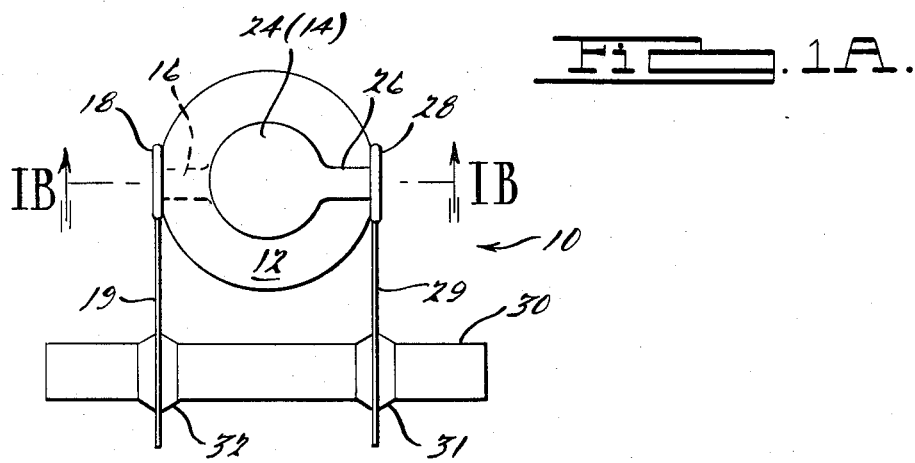
FIG. 1A is an elevational view of the piezoelectric sensing device used for measuring viscosity in the present invention.
Figure 1B:
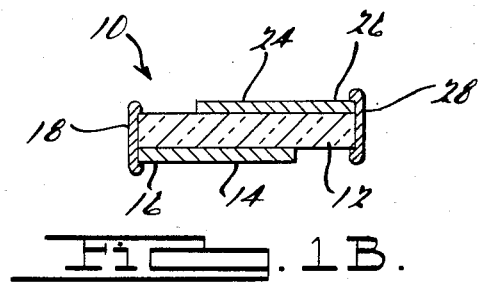
FIG. 1B is a cross-sectional view, along lines IB—IB, of the sensing device shown in FIG. 1A.

The preferred embodiment of the piezoelectric sensor element 10 for measuring the viscosity of liquids is shown in FIGS. 1A and 1B. The sensor element 10 comprises a disc shaped crystal 12, which is AT cut quartz. The crystal 12 is made to vibrate in a thickness-shear mode by applying an AC electric field across the thickness dimension. In order to facilitate the thickness-shear vibrational mode, a pair of electrodes 14 and 24 are bonded to the opposing surfaces of the crystal 12. The electrodes are thin films of inert, electrically conductive material such as aluminum, nickel or gold. They are located on the surfaces of the crystal 12 in such a manner as to define a central area of overlap through which the field will be applied. In this embodiment, the area of overlap is concentric with the center of the circular surfaces of the crystal 12 and has a lesser diameter than that of the crystal surfaces. Each electrode 14 and 24 has a portion, 16 and 26 respectively, which extends to the outer edge of the crystal 12.

Lead wires 19 and 29 provide suspension support to the piezoelectric sensor 10 and a conveyance for the electrical energy that is used to drive the piezoelectric sensor 10 in its thickness-shear mode. The lead wire 19 is electrically and physically connected at 18 to the outer edge of the crystal 12 and to the extension 16. Similarly, lead wire 29 is physically and electrically connected at 28 to the opposite edge of the crystal 12 and the extension 26. An electrical insulator support member 30 suspends the entire sensor 10 by providing seals or electrical feed-through connections 31 and 32 to the respective lead wires 29 and 19.

Figure 2:
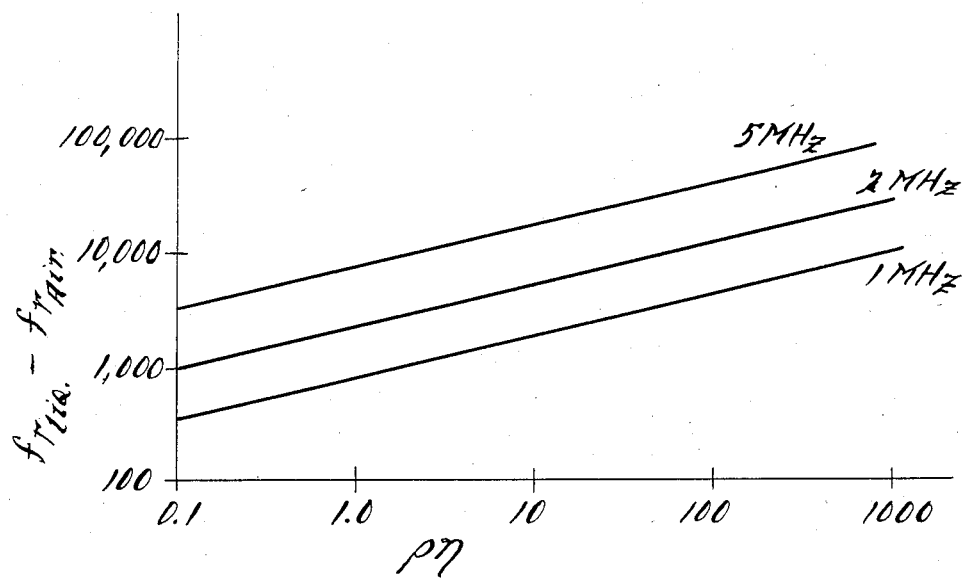
FIG. 2 is a calibration chart which allows one to determine the viscosity of a liquid after measurements using the present invention are made.

FIG. 2 is a calibration-measurement chart which was prepared utilizing the present invention and samples having known values of viscosity. On the ordinant of the chart, values of viscosity are logarithmically scaled in values of $\rho\eta$ (density $\times$ viscosity in centipoise). The abscissa of the chart is in units of Hertz on logarithmic scale indicating the difference between the resonant frequency of the sensor in liquid and the resonant frequency of the sensor in air. The calibration lines labeled 1 MHz, 2 MHz and 5 MHz correspond to differently rated piezoelectric sensor elements that have corresponding resonant frequencies in air.

In use, the piezoelectric sensor 10 is driven electrically in an air medium until it reaches its resonant frequency. The frequency of the driving oscillator should correspond to the rated frequency of the element. The sensor element is then placed in the liquid medium to be measured and the element is again electrically energized. The frequency of energization is changed until the sensor element 10 reaches its new resonant frequency. The difference in the resonant frequency in the liquid and that in air is plotted on the calibration-measurement chart in FIG. 2 along the rated frequency line to find a value of viscosity for the measured liquid.

Figure 3:
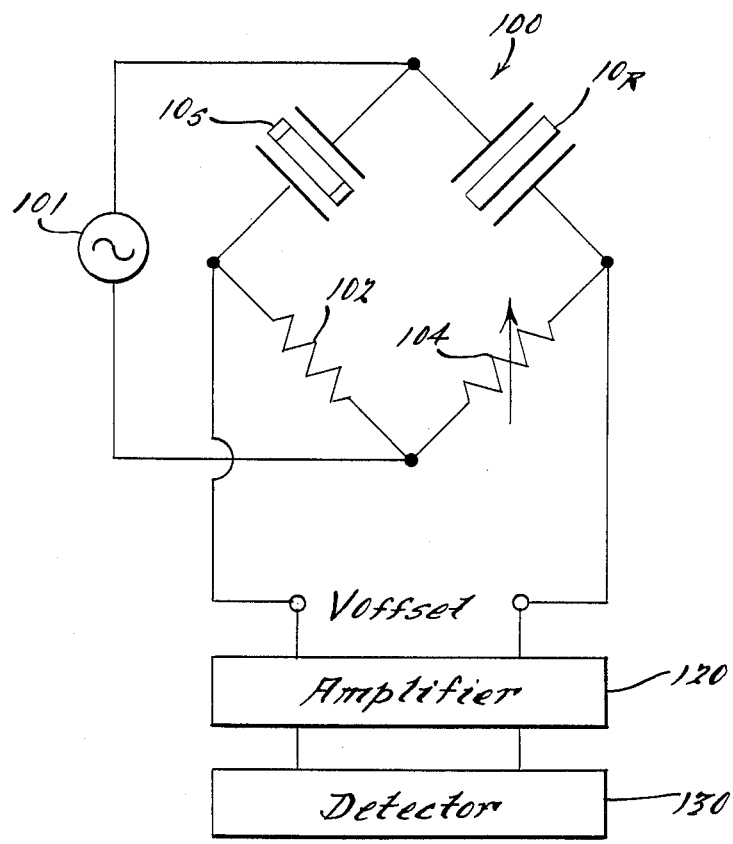
FIG. 3 is a circuit diagram illustrating a double element bridge for sensing the resonant frequency of the thickness-shear mode crystal used in the present invention.
Figure 4:
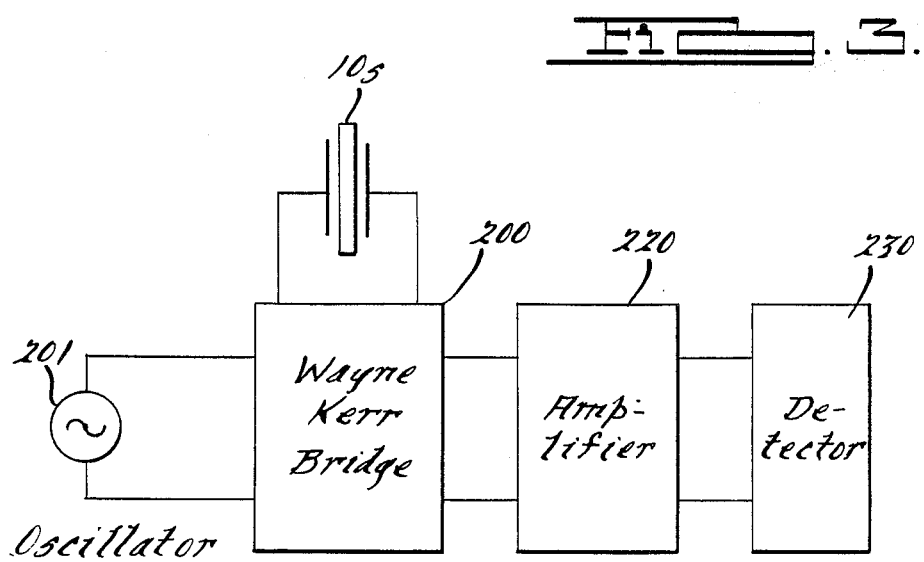
FIG. 4 is a block diagram illustrating the use of a Wayne-Kerr bridge for sensing the resonant frequency of the thickness-shear mode crystal used in the present invention.

Circuits shown in FIGS. 3 and 4 may be used in the method to detect when the sensor reaches its resonant frequency level.

In FIG. 3, a double element bridge is utilized to make the appropriate measurements. In the double element bridge circuit, a reference crystal $10_R$ resides in one leg of the bridge 100 and is suspended in a reference medium that may be air or a standard liquid of which the viscosity is known. A sampling element $10_S$ is the shear mode piezoelectric sensing element, as shown in FIGS. 1A and 1B and preferrably contains an identical air resonant frequency rating to crystal $10_R$. Resistor 102 and adjustable resistor 104 reside in separate legs of the bridge 100 and are used to balance the bridge. A highly stable oscillator 101 is connected across bridge 100 to drive the crystals $10_R$ and $10_S$ in parallel. The offset voltage is measured across the medial portions of the bridge 100, between each crystal and its associated resistor, by an amplifier 120. The amplifier 120 is output to a detector 130 which provides visual indication of the offset voltage so that the operator may determine when the piezoelectric elements are at resonance.

The oscillator 101 must be sufficiently stable and accurate so as to allow for the detectability between resonance and antiresonance of the piezoelectric elements. For instance, in air, the difference in frequency between resonance and antiresonance may be on the order of 100 Hz for a 2 MHz AT cut quartz crystal. On the other hand, in liquids, the difference between the maximum and minimum impedance frequency may range from 500 Hz to 10,000 Hz. Therefore, an oscillator stability of approximately 1–10 Hz is necessary to be acceptable. In addition, the frequency range of the electrical oscillator must be accurately adjustable over the range of resonant frequencies defined by the piezoelectric element in air to the element submerged in the most viscous solution to be measured.

When measuring viscosities with this technique, one needs a very sensitive monitoring circuit. Typically, the change in impedance from ON-resonance to OFF-resonance has a difference which decreases with increasing liquid viscosities. Using a bridge circuit which is balanced OFF-resonance, the signal for frequencies OFF-resonance is greatly reduced while the signal for ON-resonance remains essentially unchanged. This allows for substantial resolution of the signal through amplification and clearer identification of the resonant frequency.

Initially the double element circuit shown in FIG. 3 must be nulled. This may be achieved by setting both piezoelectric elements $10_R$ and $10_S$ in an air medium or a standard liquid and adjusting the frequency of oscillator 101, to a point approximately 0.2% above the resonant frequency. Then, resistor 104 is adjusted until the minimum offset voltage is achieved and detected. For measurement, the reference crystal $10_R$ may be left in the air medium or submerged in the standard liquid having a known viscosity. The measuring element $10_S$ is submerged in the liquid to be measured. As the frequency of the oscillator is varied, the offset voltage of the double element bridge 100 will show two peaks. One of the peaks corresponds to the resonance of the element $10_R$ and the other will correspond to the resonance of the element $10_S$ in the liquid being measured. If the reference crystal $10_R$ is in air, the difference between the two resonant frequencies is that needed to calculate the viscosity from the chart shown in FIG. 2.

In FIG. 4, a Wayne-Kerr bridge circuit 200 is utilized with a voltage control oscillator 201, similar to that discussed above. Again, the bridge is adjusted to give a minimum offset voltage at approximately 0.2% above the resonant frequency. The piezoelectric element $10_S$ is submerged in the liquid to be measured and the oscillator 201 is changed until the resonant frequency of the crystal is detectd, i.e., until the maximum offset voltage is obtained. The difference in measured resonant frequencies is then used with the chart shown in FIG. 2 to determine the viscosity of the liquid.

While the above discussion of viscosity measurements of liquid assumes that the liquids are nonconducting, with slight modification, the apparatus could be employed to also measure the viscosity of conducting liquids. Specifically, one electrode could be coated with a thin film of insulator material to prevent current leakage through the liquid.

It will be apparent that many modifications and variations may be implemented without departing from the scope of the novel concept of this invention. Therefore, it is intended by the appended claims to cover all such modifications and variations which fall within the true spirit and scope of the invention.

I claim:

1. An apparatus for measuring the viscosity of liquids comprising:
    piezoelectric means containing a thickness shear mode crystal with opposing major surfaces, opposing electrodes mounted on said major surfaces and lead wires correspondingly connected to said electrodes for suspending said thickness shear mode crystal and conveying electrical drive energy to said electrodes;
    energization means for supplying AC electrical drive energy to said piezoelectric means; and
    detection means for monitoring electrical characteristics of said piezoelectric means when driven by said energization means.

2. A viscosity measuring apparatus as in claim 1, wherein said thickness shear mode crystal has a circular disc shape and said electrodes are thin films of conducting material disposed on portions of said circular major surfaces.

3. A viscosity measuring apparatus as in claim 2, wherein said opposing electrodes are substantially circular in shape but of a lesser diameter than said thickness shear mode crystal and concentrically mounted on said thickness shear mode crystal so as to provide an outer circular ring on said thickness shear mode crystal in which the electrodes are not opposing.

4. A viscosity measuring apparatus as in claim 3, wherein said opposing electrodes each have a portion extending from said circular shape in opposite directions to diametrically opposite edges of said thickness shear mode crystal and said lead wires are connected to said opposite edges of said thickness shear mode crystal and to said extended portions of said electrodes.

5. A viscosity sensing apparatus as in claim 4, wherein said energization means has an adjustable frequency output and said detection means indicates when the thickness shear mode crystal has reached a resonant vibrational state in response to said energization means providing a known frequency of drive energy to said crystal.

6. A viscosity measuring apparatus as in claim 1, wherein said piezoelectric means further includes an insulating mount means for supporting said lead wires.

7. A method for measuring the viscosity of liquids comprising:
    providing piezoelectric means containing a thickness shear mode crystal with opposing major surfaces, opposing electrodes mounted on said major surfaces and lead wires correspondingly connected to said electrodes for suspending said thickness shear mode crystal and conveying electrical drive energy to said electrodes;
    providing energization means for supplying AC electrical drive energy to said piezoelectric means; and
    providing detection means for monitoring electrical characteristics of said piezoelectric means when driven by said energization means.

8. A method of measuring viscosity as in claim 7, wherein said thickness shear mode crystal is provided in a circular disc shape and said electrodes are provided as thin films of conducting material disposed on portions of said circular major surfaces.

9. A method of measuring viscosity as in claim 8, wherein said opposing electrodes are provided as substantially circular in shape but of a lesser diameter than said thickness shear mode crystal and concentrically mounted on said thickness shear mode crystal so as to provide an outer circular ring on said thickness shear mode crystal in which the electrodes are not opposing.

10. A method of measuring viscosity as in claim 9, wherein said opposing electrodes are each provided to have a portion extending from said circular shape in opposite directions to diametrically opposite edges of said thickness shear mode crystal and said lead wires are connected to said opposite edges of said thickness shear mode crystal and to said extended portions of said electrodes.

11. A method of measuring viscosity as in claim 10, wherein said energization means is provided with an adjustable frequency output and said detector means is provided to indicate when the thickness shear mode crystal has reached a resonant vibrational state in response to said energization means providing a known frequency of drive energy to said crystal.

* * * * *